US011910514B2

(12) United States Patent
Chianura et al.

(10) Patent No.: US 11,910,514 B2
(45) Date of Patent: Feb. 20, 2024

(54) APPARATUS AND METHOD TO NEUTRALIZE STATIC ELECTRICITY PRESENT ON THE SURFACE OF CONTAINERS AND/OR CONTAINER-HOLDING TRAYS

(71) Applicant: I.M.A. INDUSTRIA MACCHINE AUTOMATICHE S.P.A., Ozzano dell'Emilia (IT)

(72) Inventors: Mattia Chianura, Ozzano dell'Emilia (IT); Sergio Manera, Ozzano dell'Emilia (IT)

(73) Assignee: I.M.A. Industria Macchine Automatiche S.P.A., Ozzano dell'Emilia (IT)

( * ) Notice: Subject to any disclaimer, the term of this patent is extended or adjusted under 35 U.S.C. 154(b) by 233 days.

(21) Appl. No.: 17/641,486

(22) PCT Filed: Sep. 1, 2020

(86) PCT No.: PCT/IT2020/050211
§ 371 (c)(1),
(2) Date: Mar. 9, 2022

(87) PCT Pub. No.: WO2021/048883
PCT Pub. Date: Mar. 18, 2021

(65) Prior Publication Data
US 2022/0312576 A1    Sep. 29, 2022

(30) Foreign Application Priority Data

Sep. 11, 2019   (IT) ...................... 102019000016091

(51) Int. Cl.
*H05F 3/06*      (2006.01)
*B01L 3/00*      (2006.01)
(Continued)

(52) U.S. Cl.
CPC .............. *H05F 3/06* (2013.01); *B01L 3/5082* (2013.01); *B01L 9/06* (2013.01); *G01G 23/00* (2013.01);
(Continued)

(58) Field of Classification Search
CPC ....................... G01N 2035/00297; H05F 3/06
See application file for complete search history.

(56) References Cited

U.S. PATENT DOCUMENTS

2006/0137760 A1* 6/2006 Dubois ................. B65B 1/32
                                                   141/1
2018/0149512 A1* 5/2018 Meyer ..................... B05B 1/06

FOREIGN PATENT DOCUMENTS

EP         3327409 A1     5/2018
WO    2018/177800 A1    10/2018

OTHER PUBLICATIONS

International Search Report and Written Opinion for PCT Patent Application No. PCT/IT2020/050211 dated Nov. 20, 2020. 11 Pages.

* cited by examiner

*Primary Examiner* — Jared Fureman
*Assistant Examiner* — Christopher J Clark
(74) *Attorney, Agent, or Firm* — McAndrews, Held & Malloy, Ltd.

(57) ABSTRACT

Apparatus to neutralize static electricity present on the surface of containers (100; 10') and/or of nests (200; 300) comprising a plurality of seatings (212; 312) according to a positioning matrix (M1) and able to receive, resting on them, an ordered group of said containers (100; 100), wherein the apparatus comprises an extraction member (15) configured to engage at least one part of said ordered group of containers (100; 100'), in order to perform at least one relative lifting movement with respect to the nest (200; 300) so as to (Continued)

at least partly extract the containers (100; 100') engaged from the respective seatings (212; 312), and at least one ionizing device (19) configured to be relatively mobile with respect to the extracted containers and/or with respect to the nest (200; 300), while said group of containers (100; 100') extracted is in said raised condition, along a path that develops in the proximity of the containers (100; 100') extracted and/or in the proximity of said nest (200; 300), so as to ionize the surrounding space and neutralize static electricity present on the surface of the containers (100; 100') in the raised condition and/or of the nest (200; 300).

15 Claims, 10 Drawing Sheets

(51) Int. Cl.
- *B01L 9/06* (2006.01)
- *G01N 35/04* (2006.01)
- *G01G 23/00* (2006.01)
- *G01N 35/00* (2006.01)

(52) U.S. Cl.
CPC ........ *G01N 35/04* (2013.01); *B01L 2200/028* (2013.01); *B01L 2200/143* (2013.01); *G01N 2035/00297* (2013.01); *G01N 2035/041* (2013.01); *G01N 2035/0418* (2013.01)

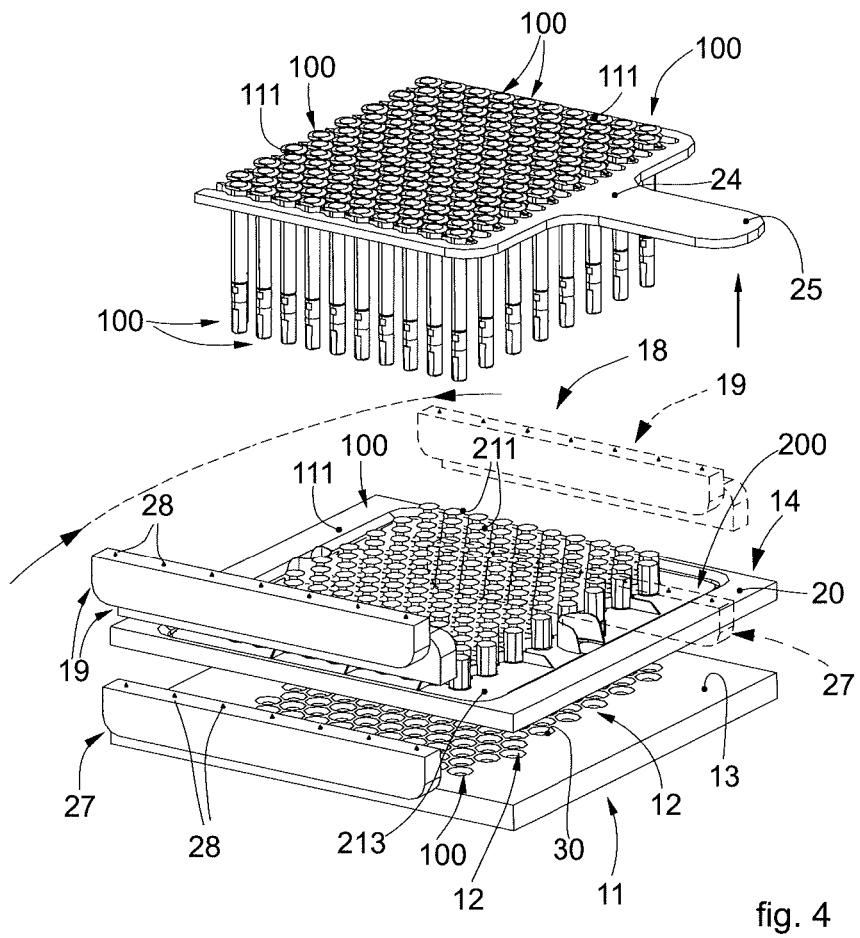
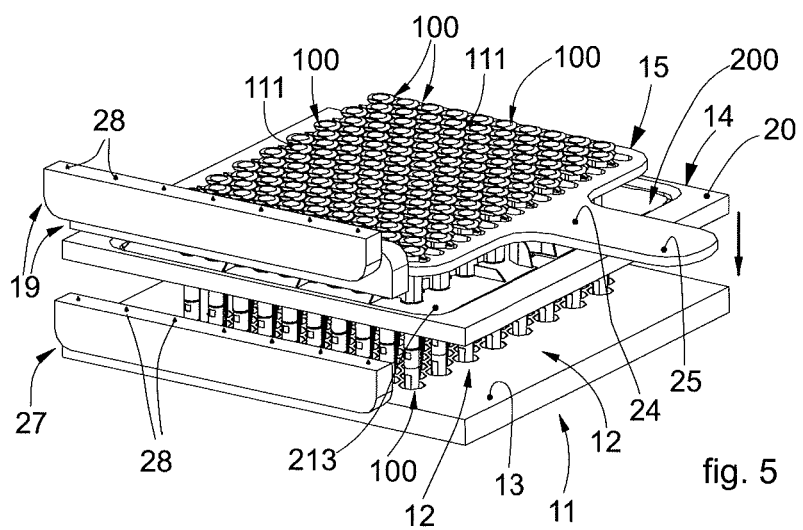

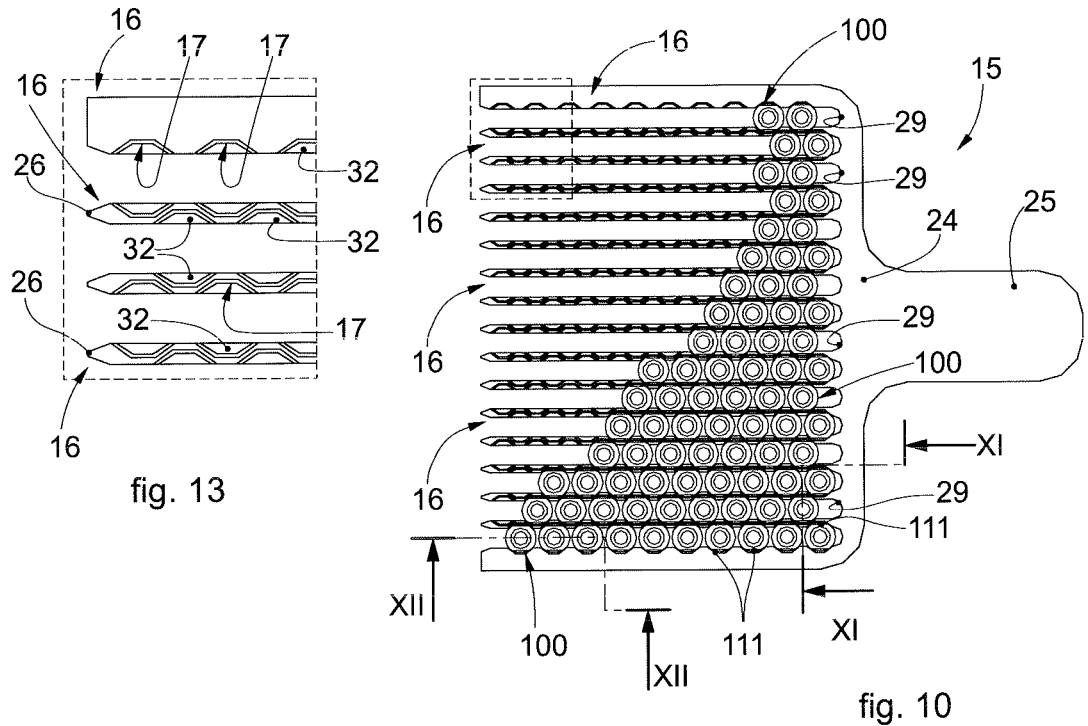
fig. 13
fig. 10
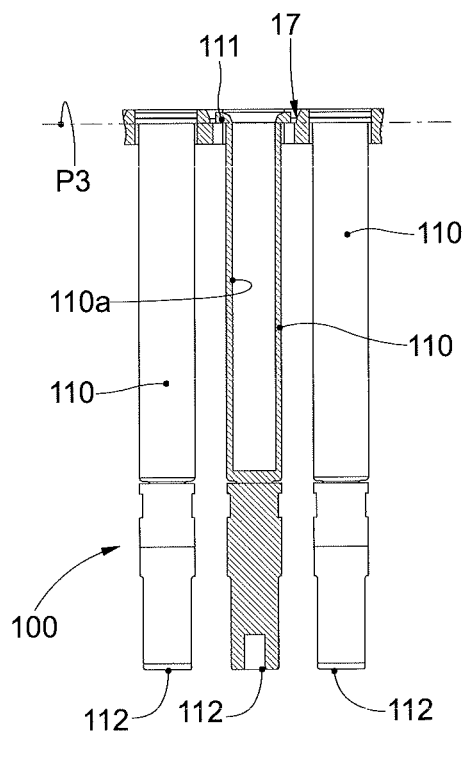
fig. 11
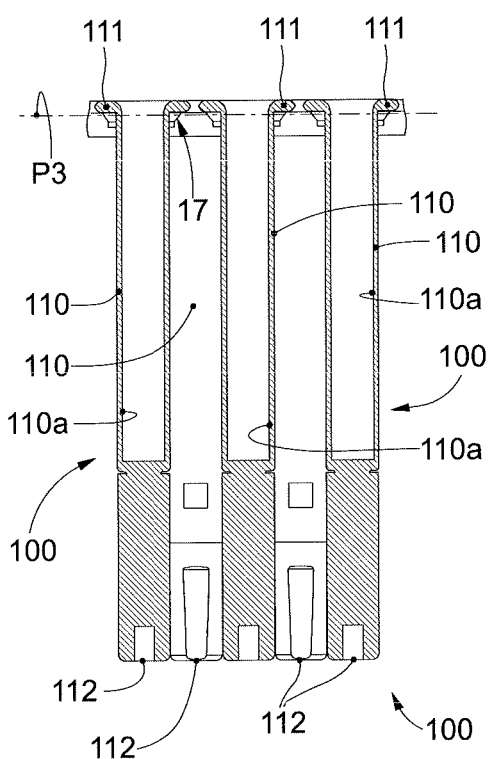
fig. 12

APPARATUS AND METHOD TO NEUTRALIZE STATIC ELECTRICITY PRESENT ON THE SURFACE OF CONTAINERS AND/OR CONTAINER-HOLDING TRAYS

CROSS-REFERENCE TO RELATED APPLICATIONS

This application is a national stage application of International Application No. PCT/IT2020/050211, having an International filing date of Sep. 1, 2020, which claims priority to Italy Application No. 102019000016091, filed Sep. 11, 2019. The entire disclosures of the aforesaid applications are incorporated herein by reference.

FIELD OF THE INVENTION

The present invention concerns an apparatus and a method to neutralize static electricity present on the surface of containers and/or container-holding trays, in particular both when the containers are empty and also when they are filled with at least one product or substance. By the term product or substance we mean any liquid, semi-solid, gelatinous or solid composition, in which case it can be in powder or in grains and can be of vegetable and/or animal and/or chemical origin. The containers to be weighed can be temporarily housed in "nests" or container-holding trays, or in similar and/or comparable support means, in predetermined positions of a matrix of housing seatings. By way of non-restrictive example, the apparatus and method in accordance with the present invention can be used in the field of pharmaceuticals, cosmetics, health, chemicals and foods.

BACKGROUND OF THE INVENTION

It is known that in the pharmaceutical, health, chemical or industrial fields, or more generally in technical-scientific fields, there is a need to weigh containers, pre-filled with a precise quantity of a certain product, inside suitable weighing stations. Examples of some solutions known in the state of the art are described by patent documents EP 3.327.409 and WO 2018/177800.

The containers to be weighed can have different shapes and sizes, from test tubes to small ampoules for medicines, with a capacity of a few milliliters, or syringes, or Carpules®, that is, ampoules or cartridges containing medication liquid to be inserted in a syringe, to more capacious containers, such as bottles, flasks or other, with capacities greater than one liter, able to contain fluid products, in particular liquids, or solid and powdered or gel products.

In particular, in the chemical, pharmaceutical and healthcare sectors there is often the need to fill the containers as above with products according to a predefined dosage which, due to the nature of the product introduced and the function which that product is intended to perform, allows reduced variations, contained within predefined fields.

Very often, the product to be weighed is dosed inside the containers in small quantities. Consequently, even small deviations in the measured weight value with respect to the real weight value can generate significant errors that can lead to dangerous consequences for the consumer or patient, especially if this product is applied in the pharmaceutical and healthcare fields.

In some applications known in the state of the art, the containers can be positioned in suitable seatings of a container-holding tray which, in this specific sector, is commonly called a "nest".

The filling of the containers takes place in filling systems by means of filling machines provided with filling nozzles which, in relation to the type of product treated, are suitable to deliver a precise quantity of product into the container.

As we said, the verification of the mass of the product introduced into each container is fundamental, since the objective is to introduce a quantity of product corresponding to the expected dosage.

For this purpose, it is known to use weighing systems, associated or not with the filling systems as above, which use weight detectors, or load cells, suitable to detect the weight of the containers both when they are empty (tare), and also when they are filled (gross weight).

According to a first approach, the containers are removed one by one from the seatings to be individually subjected to the filling and/or weighing operations.

According to another approach developed by the present Applicant, the operations to fill and/or weigh the containers can be performed even without removing the containers from the rack. In this case, the rack is manipulated with movement means which allow to position the rack, and in particular the container to be filled and/or weighed, in correspondence with a filling nozzle and/or a weighing device.

Weighing systems of this type are described, for example, in document WO2018/019985, in the name of the present Applicant.

In particular, WO2018/019985 describes a weighing system for containers positioned in suitable housing seatings disposed in a rack, movable by means of a manipulator arm toward a load cell.

The positioning of the single container on the load cell, both before and after filling, in order to detect the tare and gross weight, takes place without the container moving from the rack and from the housing seating.

The weighing system also comprises a weighing device, provided with a load cell, and suitable to accommodate, at least for the time needed for the weighing operation, the single container or part of it. The weighing devices described in WO2018/019985 are provided with a suitably shaped seating to house at least part of the container involved in the weighing operation.

In this context, it should be noted that normally, before the weighing station of the filled containers, a plurality of processing stations can be provided, such as for example a storage station for the empty containers, one or more possible weighing stations for each empty container, a station for filling containers or other.

The movement of the containers from one station to another is usually carried out with mechanical and motorized transport devices or apparatuses, which comprise, for example, conveyor belts, turntables, or carousels, gears, chains, sliders, lifters, mechanical arms, possibly robotic, and other mechanical members.

On this point, the Applicant has found in general that, during movement from one station to another, electrostatic charges can accumulate on the surfaces of the containers and/or on the container-holding tray, for example both due to phenomena of reciprocal rubbing or of rubbing against surfaces, metal or non-metal, of machine components in which the weighing system is integrated, and also due to phenomena of friction that are generated with the transport apparatuses.

The containers and/or the container-holding tray can be electrostatically charged also during the production step and/or during the positioning of the containers in the container-holding tray.

One disadvantage of the accumulation of electrostatic charges on the containers and/or on the container-holding tray is that, during the weighing operation, the presence of electrostatic charges can affect the measurement of the weight: the electrostatic attraction between charges, in fact, generates a vertical component that is added to or subtracted from the weight force. Consequently, the measurement detected by the weighing device is erroneous, providing an untrue weight value and therefore an inaccurate measurement of the mass.

This problem is quite serious, especially when the containers are weighed, together or in groups, without being extracted from the container-holding tray as described above, for example according to WO2018/019985 in the name of the present Applicant. In fact, the presence of attractive/repulsive electrostatic forces generated during functioning can cause errors in measurement, long stabilization times of the measurement and non-repeatability of the measurement. It has been found that attractive/repulsive electrostatic forces are generated between the containers and the nest, or between the containers themselves, or between the containers and parts of the machine, or also between the nest and parts of the machine. Furthermore, the electrostatic charge causes phenomena of attraction between parts of the machine or the container or the container-holding tray and particles present in the air. This phenomenon is generally undesirable, especially in the food and pharmaceutical sector.

There is therefore a need to provide an apparatus to neutralize the static electricity present on the surface of containers and/or container-holding trays that can overcome at least one of the disadvantages of the state of the art.

In particular, one purpose of the present invention is to provide an apparatus that allows to eliminate the electrostatic charges present and/or accumulated on the containers and/or on the container-holding tray before the operation to weigh them.

Another purpose is to perfect a method to neutralize static electricity present on the surface of containers and/or container-holding trays that uses the apparatus as above.

The Applicant has devised, tested and embodied the present invention to overcome the shortcomings of the state of the art and to obtain these and other purposes and advantages.

SUMMARY OF THE INVENTION

The present invention is set forth and characterized in the independent claims. The dependent claims describe other characteristics of the present invention or variants to the main inventive idea.

In accordance with the above purposes, the present invention concerns an apparatus to neutralize static electricity present on the surface of containers and/or container-holding trays or nests, in which an ordered group of containers is disposed. The containers in question have a body that develops along a main axis of longitudinal development of the container, which includes a closed base end and an opposite open head end.

The apparatus comprises the container-holding tray or nest as above, which has a plurality of seatings disposed according to an ordered matrix, each seating being configured to house, resting on it, a respective container of the ordered group of containers, and developing along an axis of symmetry substantially vertical and parallel to, preferably coincident with, the main axis of the container housed in the seating, the axes of symmetry of the plurality of seatings being reciprocally parallel.

The apparatus comprises extraction means, configured to engage at least one part of the ordered group of containers housed in the container-holding tray as above. The extraction means are configured to perform at least one relative lifting movement with respect to the container-holding tray, so as to at least partly extract from the respective seatings of the container-holding tray at least one part of the ordered group of containers previously engaged. The extraction means are also configured to maintain this part of the ordered group of containers extracted from the respective seatings in a raised condition, so that the seatings of the container-holding tray, previously occupied by the containers, are left at least partly free.

According to one aspect of the present invention, the extraction means are configured as an extraction member comprising one of a plurality of inter-spaced arms, parallel to each other and defining at least one gripping loop configured to house the containers. The extraction member is configured to perform, before the relative lifting movement as above, at least one relative engagement movement with respect to the container-holding tray, in order to house the at least one part of the ordered group of containers as above, laterally aligning the at least one gripping loop with at least one respective row of the ordered matrix of seatings, and moving the at least one gripping loop in a direction of engagement, which is transverse with respect to the axes of symmetry of the seatings as above, so as to house and hold at least such part of the ordered group of containers in the at least one gripping loop.

With the term "transverse" we mean that the direction of engagement is incident with respect to the axes of symmetry of the seatings, coherently with the lateral alignment of the gripping loop. In possible embodiments, the direction of engagement is incident with respect to the axes of symmetry of the seatings according to an inclined directrix, for example from above or below, comprising at least one component of vertical motion. In another alternative embodiment, the direction of engagement is perpendicular to the axes of symmetry of the seatings, since it is without any component of vertical motion whatsoever.

The apparatus also comprises at least one ionizing device configured to be relatively mobile with respect to the containers extracted and/or with respect to the container-holding tray, while the at least one part of the group of containers extracted is in the raised condition and the container-holding tray has the seatings left at least partly free by the respective containers extracted, along a path that develops in the proximity of the containers extracted and/or in the proximity of the container-holding tray or nest, so as to ionize the surrounding space and neutralize static electricity present on the surface of the containers in the raised condition and/or of the container-holding tray or nest having the seatings left at least partly free by the respective containers.

With the expression "in proximity of", here and hereafter in the description we mean that the path as above develops in such a way as to allow the ions emitted by the ionizing device to reach the containers or the nest, the static electricity of which is to be ionized. Specifically, it will be clear to the person of skill in the art that the path of the ionizing device can be articulated, at least partly, even at a certain distance from the containers or nest, provided that this distance is such as to allow an effective electrostatic interaction between the objects to be electrostatically neutralized and the ions emitted by the ionizing device.

Some embodiments of the present invention also concern a method to neutralize static electricity present on the surface of containers and/or container-holding trays or nests in which the containers are disposed. The method comprises the following steps:

preparing an ordered group of containers, each having a body which develops along a main axis of longitudinal extension of the container, the body including a closed base end and an opposite open head end;

preparing a container-holding tray or nest, having a plurality of seatings disposed according to an ordered matrix, each seating being configured to house, resting on it, a respective container of the ordered group of containers, and developing along an axis of symmetry substantially vertical and parallel to, preferably coincident with, the main axis of the container housed in the seating, wherein the axes of symmetry of the plurality of seatings are reciprocally parallel;

preparing extraction means configured as an extraction member suitable to engage and move at least one part of the ordered group of containers housed in the nest as above, wherein the extraction member is configured as previously described;

preparing at least one ionizing device configured to be relatively mobile with respect to the containers and/or with respect to the nest;

extracting at least one part of the group of containers as above from respective seatings of the nest occupied by the containers resting on them, by moving the extraction member with a relative lifting movement with respect to the nest so as to at least partly extract, from the respective seatings of the nest, the at least one part of the ordered group of containers;

reaching a raised condition in which the at least one part of the ordered group of containers extracted from the respective seatings is maintained stationary in a position such as to leave the respective seatings of the container-holding tray previously occupied by the extracted containers at least partly free;

neutralizing static electricity present on the surface of the containers in the raised condition and/or of the container-holding tray or nest, by means of at least one ionizing device, by operating a relative motion of the ionizing device with respect to the containers extracted and/or with respect to the nest, while the at least one part of the ordered group of containers extracted is in the raised condition and the nest has the seatings left at least partly free by the respective containers extracted, along a path that develops in the proximity of the containers in the raised condition and/or of the container-holding tray or nest, so as to ionize the surrounding space and neutralize static electricity present on the surface of the containers in the raised condition and of the container-holding tray or nest having the seatings left at least partly free by the respective containers extracted.

According to one aspect, the method of the present invention provides that, before the extracting step, a step of engaging the at least one part of the containers is performed by moving the extraction member with relative movement toward the nest, laterally aligning the at least one gripping loop with at least one respective row of the ordered matrix of seatings and moving the at least one gripping loop in a direction of engagement transverse with respect to the axes of symmetry of the seatings, so as to house and hold the at least one part of the ordered group of containers in respective gripping loops to then carry out the step of extracting the at least one part of the ordered group of containers housed and held in the at least one gripping loop.

ILLUSTRATION OF THE DRAWINGS

These and other aspects, characteristics and advantages of the present invention will become apparent from the following description of some embodiments, given as a non-restrictive example with reference to the attached drawings wherein:

FIGS. 2-7 represent, overall, a possible operating sequence of the functioning of the apparatus of FIG. 1;

FIG. 10 is a top plan view of an extraction member which supports, by way of example, a plurality of containers;

FIG. 11 is a section along line XI-XI of FIG. 10;

FIG. 12 is a section along line XII-XII of FIG. 10;

FIG. 13 shows an enlarged detail of FIG. 10;

To facilitate comprehension, the same reference numbers have been used, where possible, to identify identical common elements in the drawings. It is understood that elements and characteristics of one embodiment can conveniently be incorporated into other embodiments without further clarifications.

DESCRIPTION OF EMBODIMENTS

Figure 1:
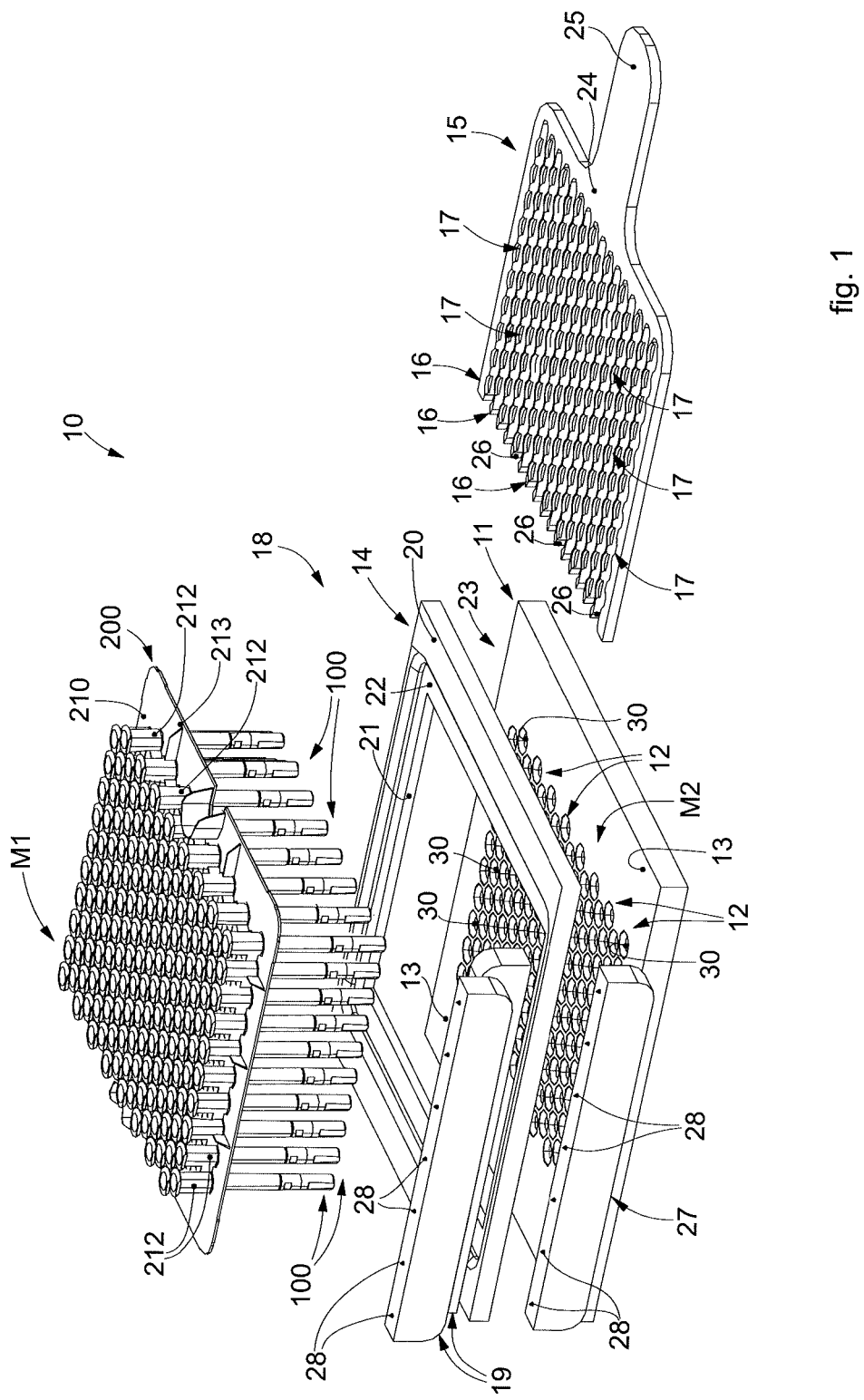
FIG. 1 is a three-dimensional view of an apparatus to neutralize static electricity present on the surface of containers and/or container-holding trays according to some embodiments.

We will now refer in detail to the various embodiments of the invention, of which one or more examples are shown in the attached drawings. Each example is supplied by way of illustration of the invention and shall not be understood as a limitation thereof. For example, the characteristics shown or described insomuch as they are part of one embodiment can be adopted on, or in association with, other embodiments to produce another embodiment. It is understood that the present invention shall include all such modifications and variants.

Before describing the embodiments, we must also clarify that the present description is not limited in its application to details of the construction and disposition of the components as described in the following description using the attached drawings. The present description can provide other embodiments and can be obtained or executed in various other ways. We must also clarify that the phraseology and terminology used here is for the purposes of description only, and cannot be considered as limitative.

Embodiments described using the attached drawings concern an apparatus, indicated as a whole with reference number 10 in the attached drawings, to neutralize static electricity present on the surface of containers 10 and/or container-holding trays, also called nests, 200.

The operation to neutralize static electricity, or electrostatic charges, present on the surface of containers 100 and/or container-holding trays 200 can hereafter also be referred to as antistatic treatment operation of containers 100 and/or container-holding trays 200 or, more briefly, antistatic treatment.

This neutralization is advantageously preparatory for a subsequent weighing operation of said containers 100 disposed in said container-holding tray 200, carried out maintaining the containers 100 present in said container-holding tray 200.

In particular, the neutralization of the electrostatic charges is advantageous to guarantee a correct measurement of the mass of the containers 100 and/or of the substance contained therein, without this weight measurement being influenced by electrostatic forces.

In accordance with some embodiments, the apparatus 10 can be used in particular to neutralize static electricity, or electrostatic charges, present on the surface of containers 100, pre-filled with a substance and pre-positioned in order to form an ordered group of containers 100 in a container-holding tray 200 according to a positioning matrix M1. The positioning matrix M1 is defined, for example, by the disposition according to a pattern with rows and columns of the containers 100 in the container-holding tray 200. This pattern provides that the containers 100 of one row are offset with respect to those of the two adjacent rows, so as to optimize the spatial disposition and guarantee that the container-holding tray 200 is able to house the largest possible number of containers 100. This spatial disposition of the containers, typical of this sector, is also called, in jargon, a "quincunx" disposition.

The apparatus 10 can also be used to neutralize static electricity present in the container-holding trays or nest 200 as above.

Each container is held, resting on it, in a respective seating 212 provided in the container-holding tray 200 and provided with a channel 211, as will be described in more detail below.

In the embodiments described below with reference to FIGS. 1-16, the seatings are configured as collars 212, each provided with a respective channel 211 into which the container is inserted, as will be described in more detail below.

Each collar 212 comprises a support edge 214 intended to receive, resting on it, a collar 111 with which each container 100 is provided.

As best seen in FIGS. 8-9 and 14-15, each collar 212 has a cylindrical wall 215 which develops around an axis of symmetry X. In this case, each channel 211 has a substantially circular cross-section. The cylindrical wall 215 has a longitudinal extension E, measured according to a directrix parallel to the axis of symmetry X, which is correlated to the sizes of the container 100. In one particular example embodiment, the collar 212 is sized so as to extend to cover a portion of the longitudinal extension of the container, at least when it is in the raised condition which will be described below.

The apparatus 10 comprises extraction means configured to engage at least one part of the ordered group of containers 100.

According to some embodiments described below, with particular reference to the attached drawings, the extraction means are configured as an extraction member 15 provided with a plurality of inter-spaced arms 16, parallel to each other and defining gripping loops 29.

Each gripping loop 29 is configured to house at least one part of the ordered group of containers 100 as above.

It is understood that in some variants, completely equivalent to the embodiments described here and shown in the attached drawings, the extraction means can comprise other members or systems, known in the state of the art and not shown, capable of extracting the containers from the nest 200. By way of a non-limiting example, the other members or systems can comprise mechanical or pneumatic systems. In one embodiment, the extraction means can comprise a plurality of suction cups, for example in a number equal to the number of containers 100 received in the container-holding tray 200, vertically mobile with respect to the latter in order to raise the containers from above.

The extraction member 15 is configured to perform at least a first relative engagement movement with respect to the container-holding tray 200, in order to engage the at least one part of the group of containers 100 disposed in the collars 212 of the container-holding tray 200, holding the containers 100 engaged in the gripping loops 29.

The extraction member 15 is configured to also perform at least a second relative lifting movement with respect to the container-holding tray 200, in order to extract the containers 100 held in the gripping loops 29 from the container-holding tray 200.

The extraction member 15 is configured to maintain the containers 100 extracted in a raised condition in which the collars 212 of the container-holding tray 200, previously occupied by the containers 100 extracted, are left at least partly free by the respective containers 100 extracted.

The extraction member 15 can be moved by means of movement devices 31 which allow its relative movement with respect to the containers 100 to be engaged and held.

In accordance with possible embodiments, the movement devices 31 can be chosen from a group comprising an automated movement device, a robotic movement device, magnetic movement devices or other known devices.

Figure 16:
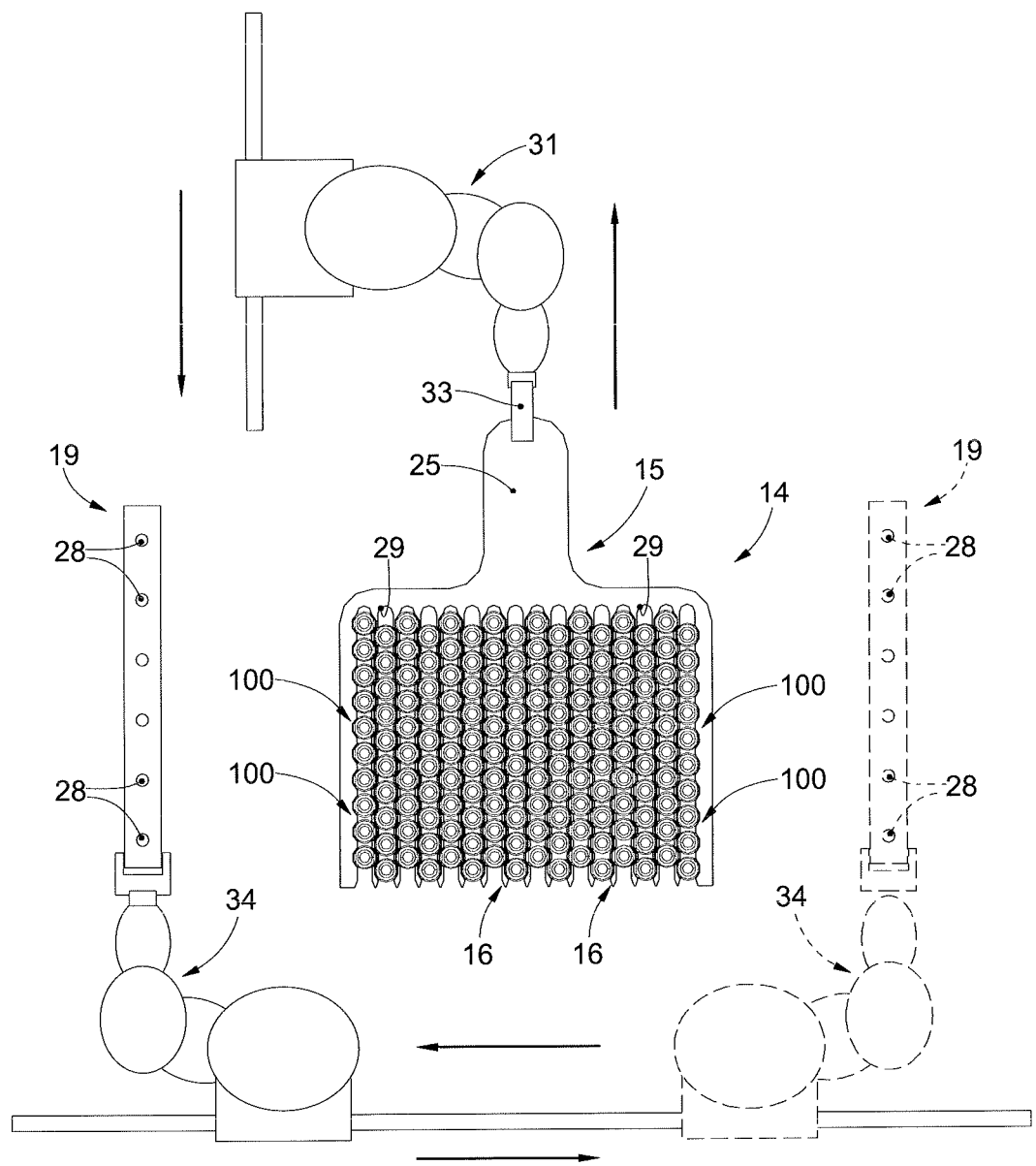
FIG. 16 shows a schematic top plan view of the apparatus of FIG. 1, which also shows the movement devices of the holding gripper and the manipulator that moves the at least one ionizing device.

In the example shown in FIG. 16, the movement devices 31 are represented in the form of an automated robotic arm mobile on at least two degrees of freedom in order to actuate the first engagement movement and the second lifting movement as above. The automated arm is provided at one end with a gripper 33 to hold and appropriately direct the extraction member 15.

In accordance with some embodiments, at least in the engagement movement as above, the extraction member 15 is configured to be operationally aligned with respect to the rows (or columns) of the positioning matrix M1, so that the gripping loops 29 at least partly house respective rows of containers 100 which are inserted in the gripping loops 29, as shown in FIG. 10.

The apparatus 10 also comprises at least one ionizing device 19 configured to be relatively mobile with respect to the containers extracted and/or with respect to the container-holding tray 200, while the group of containers 100 extracted is in the raised condition, along a path which develops in the proximity of the containers 100 extracted and/or in the proximity of the container-holding tray or nest 200, so as to ionize the surrounding space and neutralize static electricity present on the surface of the containers 100 in the raised condition and/or of the container-holding tray or nest 200.

In accordance with some embodiments, shown in FIGS. 1-9, the extraction member 15 is configured to extract at least one part of the ordered group of containers 100 held in the gripping loops 29 and to take it into the raised condition of complete extraction from the collars 212 of the container-holding tray 200, so as to create a free interspace 18 between the containers 100 extracted and the container-holding tray 200.

The at least one ionizing device 19 is configured to be relatively mobile with respect to the containers 100 in the raised condition and/or with respect to the container-holding tray 200 along a path that develops, at least partly, in the interspace 18.

Figure 15:
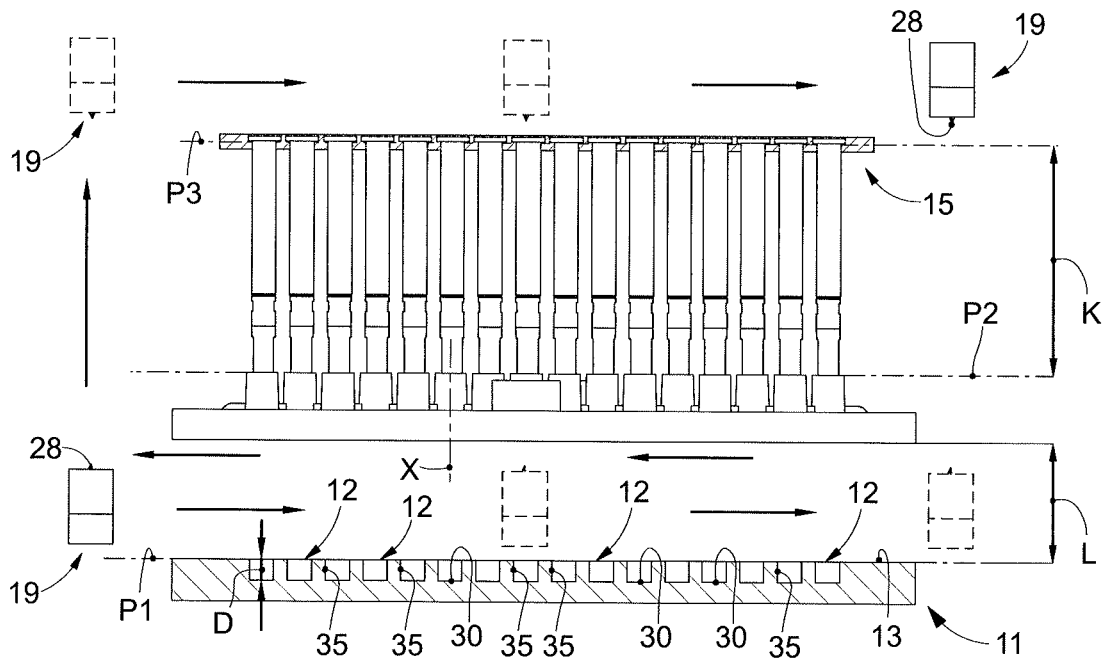
FIG. 15 shows a lateral view of an operating step of another possible operating sequence of the functioning of the apparatus of FIG. 1, in this step the containers being almost completely extracted from the container-holding tray or nest, that is, they remain only partly inside it.

In accordance with other embodiments, shown in FIG. 15, the extraction member 15 is configured to extract at least one part of the ordered group of containers 100 held in the gripping loops 29 and to take them into the raised condition of at least partial extraction of the containers 100 from the collars 212 of the container-holding tray 200. In this condition, the containers 100 can remain at least partly inside the respective channels 211 of the collars 212, but at least one part of the containers is exposed outside the collars 212 so that it can be neutralized by the action of the at least one ionizing device 19.

In accordance with some embodiments, each gripping loop 29 of the extraction member 15 comprises an array of holding seatings 17 for the containers 100 that are disposed in a manner corresponding to the positioning matrix M1, each holding seating 17 being shaped in order to support a respective container 100.

In accordance with some embodiments, the extraction member 15 comprises a transverse support 24 from which there branch off, in a direction substantially orthogonal to the transverse support 24, on one side the arms 16 and on the opposite side a gripping portion, or grip, 25 with respect to which the extraction member 15 can be manipulated, for example by an automated, even robotized, movement device, in order to perform at least the first movement of engagement of the containers 100 and the second movement of lifting the containers 100.

According to some embodiments, each gripping loop 29 is defined between two adjacent arms 16 and can be substantially U-shaped.

The width of each gripping loop 29, that is, the distance between the adjacent arms 16, is greater than the external diameter of the lateral wall 110 of the containers 100 in order to allow the insertion of the containers in the holding seatings 17. It should also be noted that the geometry of the gripping loops 29 is such that is allows to maintain the containers 100 removed in predefined and fixed positions, so as to facilitate their subsequent re-insertion into the nest 200 (FIG. 5). This is useful, in particular, if the intention is to completely extract the containers 100 from the nest 200 by means of the extraction member 15, according to the condition shown in FIG. 4.

In accordance with some embodiments, at least in said first engagement movement, the extraction member 15 is operationally aligned with respect to the rows of the positioning matrix M1 so that the gripping loops 29 comprising the holding seatings 17 are aligned with the rows of containers 100, which are suitably disposed in the resting condition and accessible with respect to a portion thereof in order to be inserted in a respective holding seating 17 shaped to support the collar 111 of a respective container 100.

According to some embodiments, the holding seatings 17 lie on a common holding plane P3 and, at least in said first engagement movement, said holding plane P3 is preferably parallel to an upper plane P2 of the container-holding tray or nest 200.

The holding plane P3 is also preferably parallel to and intermediate between the upper plane P2 and a plane on which the support edges or collars 111 of the containers 100 lie, such lying plane coinciding with the holding plane P3 at least in the second lifting movement.

In alternative embodiments, the extraction member 15 can perform the movements described above because it is disposed according to an inclined orientation so that in this case the holding plane P3 is inclined with respect to, and intersects, the upper plane P2.

Figure 8:
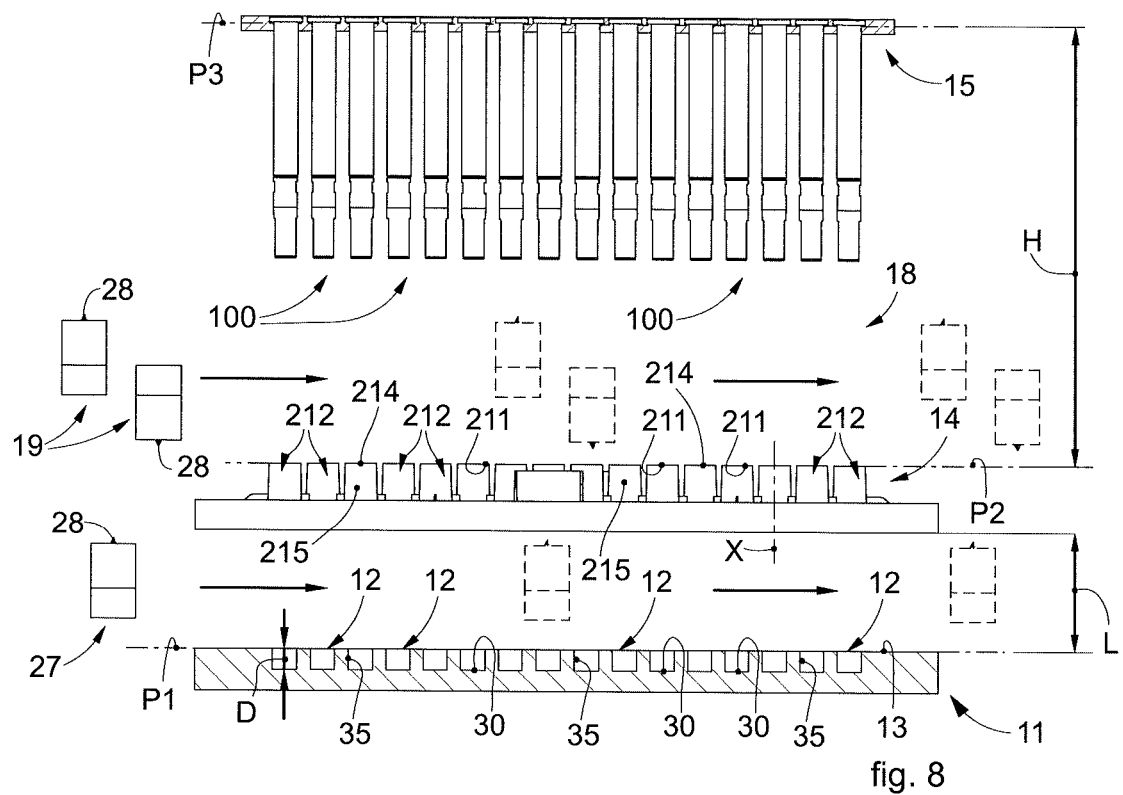
FIGS. 8 and 9 are lateral elevation views of the apparatus of FIG. 1, in which an operating step is represented according to possible other variants of implementation.
Figure 9:
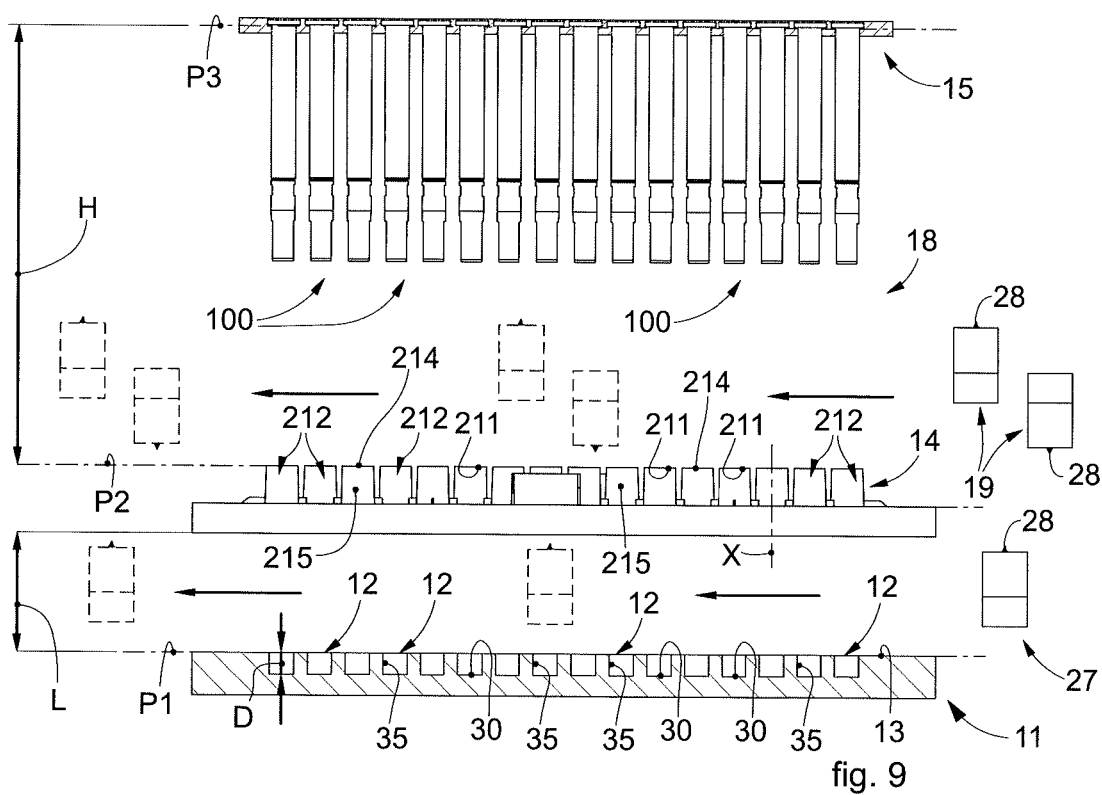

In accordance with some embodiments, shown in FIGS. 8-9, the extraction member 15, in the lifting movement to place the ordered group of containers 100 in a raised condition, defines a height H between the holding plane P3 and the upper plane P2 of the container-holding tray or nest 200 such that the containers 100 are completely extracted from the container-holding tray or nest 200 and a sufficient interspace 18 is defined to receive the at least one ionizing device 19.

In accordance with further embodiments, shown in FIG. 15, in which the extraction of the containers 100 from the container-holding tray 200 is almost complete, the extraction member 15, in said lifting movement to place the ordered group of containers 100 in a raised condition, defines a height K between the holding plane P3 and the upper plane P2 of the container-holding tray or nest 200 such that the containers 100 are almost completely extracted from the container-holding tray or nest 200 leaving a portion of each container inside the respective channel 211 of the container-holding tray 200.

In accordance with some embodiments, each arm 16 has a flared engagement end 26 so as to facilitate the alignment and centering of the containers 100 which are in the resting condition with respect to the gripping loops 29. According to some embodiments described here, the containers 100, in said resting condition, are held by the arms 16 according to a mechanical coupling with play.

In accordance with some embodiments, shown in FIG. 13, each holding seating 17 comprises respective support portions 32, facing each other from opposite sides of a same gripping loop 29, such support portions 32 being made as a recess on respective arms 16 in order to receive, resting on them, a respective container 100.

Each support portion 32 can have the shape of a circular segment, or of a portion of a polygon—for example of an octagon, a hexagon, a square or other polygon—or it can be defined by a surface subtended by a curve.

In accordance with some embodiments, shown in FIGS. 11, 12, the support portions 32 can have a flared profile in order to promote the engagement of the respective containers 100 and in particular of their support edges or collars 111.

In accordance with some embodiments, the apparatus 10 comprises a lower support base 11 provided with a bottom or contrasting surface 13 to interact with the ordered group of containers 100, before the extraction member 15 performs the first engagement movement. According to some embodiments, the contrasting surface 13 is configured to receive, in a resting condition, the ordered group of containers 100.

In accordance with some embodiments, the apparatus 10 also comprises a support member 14 disposed at a predetermined distance L with respect to the lower support base 11 and configured to maintain the container-holding tray 200 resting on it. The predetermined distance L is chosen so as to obtain the lifting of the group of containers 100 from the container-holding tray 200 when the ordered group of containers 100 is in the condition, described above, resting on the contrasting surface 13 and the container-holding tray 200 is resting on the support member 14.

In accordance with some embodiments, the contrasting surface 13 can be a flat surface, not shown, or, advantageously, a surface suitably shaped to receive, resting on it, the ordered group of containers 100.

In accordance with some embodiments, shown in FIGS. 1-9, the contrasting surface 13 is shaped and is provided with a plurality of cavities 12 disposed according to a support matrix M2, corresponding to the positioning matrix M1.

The support matrix M2 is defined for example by the disposition according to a pattern with rows and columns of cavities 12 in the lower support base 11. In particular, the number of rows and columns of cavities 12 of the support matrix M2 is equal to the number of rows and columns of the positioning matrix M1 of the containers 100 present in a respective container-holding tray 200.

Each cavity 12 has a shape substantially mating with the shape of a base end 112 of a respective container 100 opposite a collar 111 of the container 100.

Each cavity 12 is provided with a bottom wall 30 and with a lateral surface 35 which connects the bottom wall 30 to the contrasting surface 13. Each cavity 12 is configured to receive, in a resting condition, a respective container 100 of the ordered group of containers 100 present in the container-holding tray 200. It should be noted that each cavity 12 is conformed in such a way that the container 100 rests indifferently on the bottom wall 30 or, if it is not in contact with the latter, on the lateral surface 35.

Figure 2:
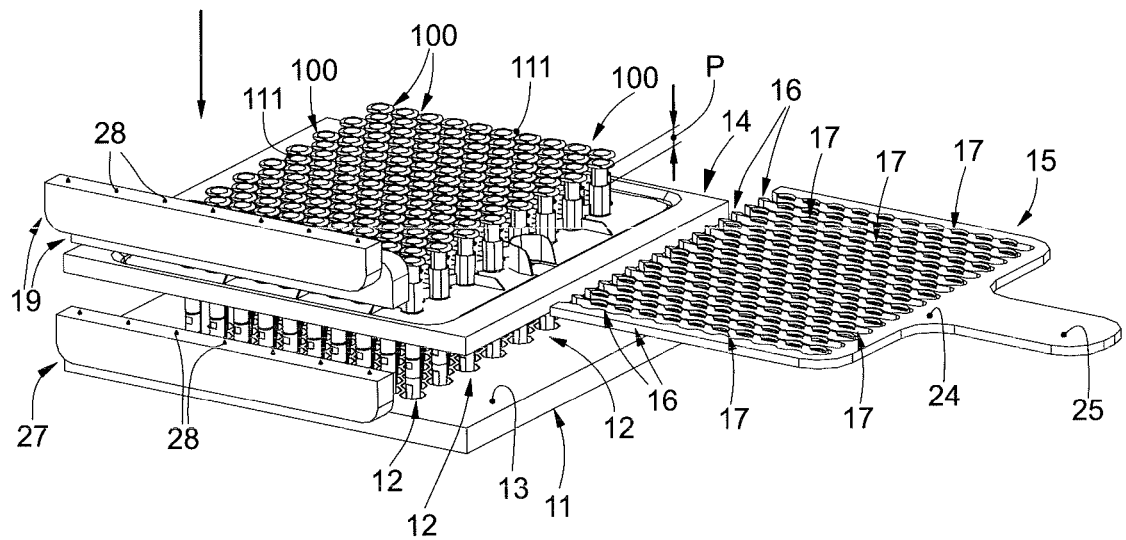
Figure 3:
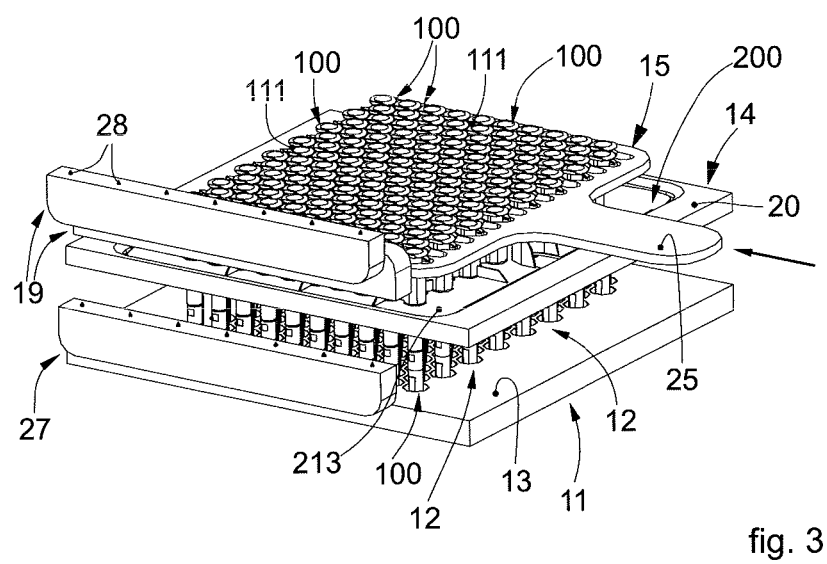

In accordance with some embodiments, shown in FIG. 2 and FIGS. 8-9, each cavity 12 has the bottom wall 30 at a depth D from an upper plane P1 on which the contrasting surface 13 is defined. This depth D is coordinated with the predetermined distance L between the support member 14 and the lower support base 11, so as to determine, when the group of containers 100 is received in the cavities 12 in the resting condition as above, and the container-holding tray or nest 200 is supported perimetrally by the support member 14, an extra-travel P to lift the collar 111 of the container 100 with respect to the plane P2, making a portion of each container 100 accessible to the extraction member 15 in order to insert each container 100 in a respective holding seating 17.

In accordance with some embodiments, each cavity 12 can be defined by a blind hole which has a flared profile, ending with the bottom wall 30, which essentially acts as a lead-in or centering surface to promote the entry of the container 100 even when a perfect vertical alignment with the container-holding tray or nest 200 is not achieved.

In accordance with some embodiments, the cavities 12 and the bottom wall 30 have a substantially circular shape, in which the diameter of one cavity 12 is greater than the diameter of the respective bottom wall 30 so as to determine the flaring necessary to promote the entry of the containers 100 as described above. In other words, each cavity 12 can have a cross-section with a slightly truncated cone shape.

In accordance with possible embodiments, not shown, each cavity 12 can be defined by a projecting portion provided with a blind hole that has a flared profile ending with the bottom wall 30.

Even if the cavities 12, and in particular the bottom wall 30, do not have a depth such as to completely support the containers 100, they are conformed in order to guarantee the necessary support to allow the containers 100 to be lifted from the container-holding tray or nest 200 by a measure corresponding to the lifting extra-travel P.

In accordance with some embodiments, the support member 14 is configured so as to be mobile away from and toward the lower support base 11, or the lower support base 11 is configured so as to be mobile away from and toward the support member 14, or both are configured so as to be reciprocally mobile away from and toward each other.

In accordance with possible embodiments, the support member 14 can be positioned at a fixed distance from the lower support base 11. For this purpose, the support member 14 can be stably attached to the lower support base 11.

The support member 14 and the lower support base 11 can be positioned, on each occasion, at the predetermined distance L from the lower support base 11 so as to allow containers 100 with even very different heights to rest on the lower support base 11.

In accordance with some embodiments, the support member 14 is shaped as a frame 20 in order to perimetrally support the container-holding tray or nest 200, defining a central aperture 21 for the passage of the ordered group of containers 100 so as to insert each container 100 in a cavity 12 below.

The frame 20 comprises a perimeter coupling edge 22 that delimits the central aperture 21 and has a shape mating with a perimeter band 213 of the container-holding tray or nest 200 without insertion channels 211. The perimeter coupling edge 22 is configured to receive, resting on it, the perimeter band 213 of the container-holding tray or nest 200 in order to maintain it supported in a stable position.

In accordance with some embodiments, the support member 14 is vertically aligned with the lower support base 11 so that the cavities 12 of the lower support base 11 are framed in the aperture 21.

In accordance with some embodiments, the container-holding trays or nests 200 can have different shapes and capacities depending on the type of containers 100 they have to support.

In accordance with some embodiments, the container-holding tray or nest 200 comprises a flat support 210 provided with a plurality of insertion channels 211 (FIG. 4), each configured to house, for example, a corresponding container 100 cooperating with it in order to support it.

The channels 211 are made, in whole or in part, through on said flat support 210 according to the positioning matrix M1 and, for example, they can be distributed regularly on offset rows, for example by a pitch corresponding to half the nominal size of each channel 211, alternately one row with respect to the adjacent one.

In accordance with some embodiments, the flat support 210 comprises collars 212 (FIG. 9), projecting vertically with respect to the flat support 210, configured to limit the oscillation of the containers 100, which they partly enclose during the movement of the container-holding tray or nest 200. Each collar 212 is provided, in correspondence with one of its upper ends, with a respective channel 211. In this case, the channels 211 can all lie on a common lying plane parallel and distanced with respect to the flat support 210.

The channels 211 can be positioned in a central zone of the flat support 210, thus defining a perimeter band 213 of the flat support 210 that is without channels 211. The perimeter band 213 can, for example, be used to support, grip, handle and move the container-holding tray or nest 200.

In accordance with some embodiments, at least in the resting condition described above, the container-holding tray or nest 200, the support member 14 and the lower support base 11 are vertically aligned.

In accordance with possible embodiments, not shown, the apparatus 10 can comprise an automated movement device, advantageously even robotic, suitable to move the container-holding tray or nest 200 inside the apparatus 10 and, in particular, to position the container-holding tray or nest 200 in correspondence with the support member 14 and define the resting condition of the containers 100.

In accordance with possible embodiments, the containers 100 can have different shapes and sizes, from small vials for medicines, with a capacity of a few milliliters, or syringes, or Carpules®, to larger containers, with capacities greater than one liter, capable of containing fluid products, in particular liquids, or solid and powdered products.

In accordance with some embodiments described here, we will refer, by way of a non-limiting example, to the type of container 100 shown for example in FIGS. 11-12, where the container 100 is configured as a syringe, with a small capacity and an elongated shape. As can easily be understood, however, the embodiments described here can also concern containers 100 of different sizes, shapes and characteristics and consequently, the shapes of the tray or nest 200 can have different sizes, geometries and characteristics.

The container 100 is provided with a lateral wall, or sleeve 110, internally delimiting a chamber 110a suitable to contain one or more substances and open upward to allow it to be filled (FIG. 12).

The container 100 is provided with a collar 111, shaped to rest on the container-holding tray or nest 200 in correspondence with the zone provided around the channel 211, so that the container 100 is positioned in a stable manner, suspended vertically from the container-holding tray or nests 200.

Preferably, the container 100 has a transverse size, that is, the external diameter of the lateral wall 110, which is correlated to the size of the channel 211. In particular, in order to be received in the channel 211, the lateral wall 110 has a diameter smaller than that of the channel 211 and, if present, also of the collar 212, but close to the sizes of the channel 211 in order to prevent the container 100 from oscillating during the movement of the container-holding tray or nest 200. The diameter of the collar 111 is preferably slightly larger than that of the lateral wall 110, in order to receive and hold the container 100 on the container-holding tray or nest 200 according to a mechanical coupling with play.

In accordance with some embodiments, the container 100 can comprise a base end 112, positioned on the opposite side with respect to the collar 111 and configured to rest on the contrasting surface 13 of the lower support base 11. In particular, the end 112 of each container 100 enters a respective cavity 12 of the lower support base 11 until it rests on its lateral surface 35. It is clear that the sizes and shape of the cavities 12 are mating with the shape of the base end 112 of the containers 100.

In accordance with some embodiments, the at least one ionizing device 19 is configured to be mobile on a movement plane, along curved or rectilinear trajectories.

In accordance with possible embodiments, the at least one ionizing device 19 is mobile along a path defined by a straight line or a curve chosen from a group comprising an arc of circumference, a parabola, an arc of an ellipse or any other curve generically defined by the trajectory of a point in the interspace 18. In any case, it is advantageous that the path that defines the movement of the at least one ionizing device 19 sweeps the totality, or substantially the totality, of the area below the containers 100 and above the support member 14 that temporarily supports the container-holding tray or nest 200.

In accordance with some embodiments, shown in FIGS. 1-9, there are at least two ionizing devices 19 disposed vertically offset so as to be facing, in said interspace 18, respectively toward the group of containers 100 in the raised condition and toward the container-holding tray or nest 200 statically supported by the support member 14.

In accordance with some embodiments, each ionizing device 19 is provided with emitters 28 configured to generate and emit positive and negative ions to neutralize the charges present on the surfaces of the containers 100 and on the container-holding tray or nest 200. In particular, the emitters 28 of the ionizing device 19 closest to the containers 100 face the containers 100; the emitters 28 of the ionizing device 19 closest to the support member 14 temporarily supporting the container-holding tray or nest 200 face the container-holding tray or nest 200.

In accordance with some embodiments, shown in FIG. 16, the apparatus 10 comprises a manipulator 34 configured to hold the at least one ionizing device 19 and move it along the path that develops in the proximity of the containers 100 in the raised condition and/or of the container-holding tray or nest 200.

The manipulator 34 is configured to move the at least one ionizing device 19 with at least two degrees of freedom, for example horizontally and vertically, with respect to the holding plane P3 and/or the plane P2 of the container-holding tray or nest 200, in order to allow the ionizing device 19 to sweep both the areas below and above the containers 100, and also the zones above and below the container-holding tray or nest 200. In accordance with some embodiments, the manipulator 34 is configured so as to be equipped with a third degree of freedom, in order to allow the rotation of the at least one ionizing device 19 around a reference axis so as to suitably turn the latter upside down, for example as shown in FIG. 14.

In accordance with some embodiments, the apparatus 10 comprises at least one other ionizing device 27 configured to be relatively mobile with respect to the containers in the raised condition and/or with respect to the container-holding tray 200 along a path that develops into another free interspace 23 between the container-holding tray 200 and the lower support base 11, when the containers 100 extracted are in the raised condition.

Figure 14:
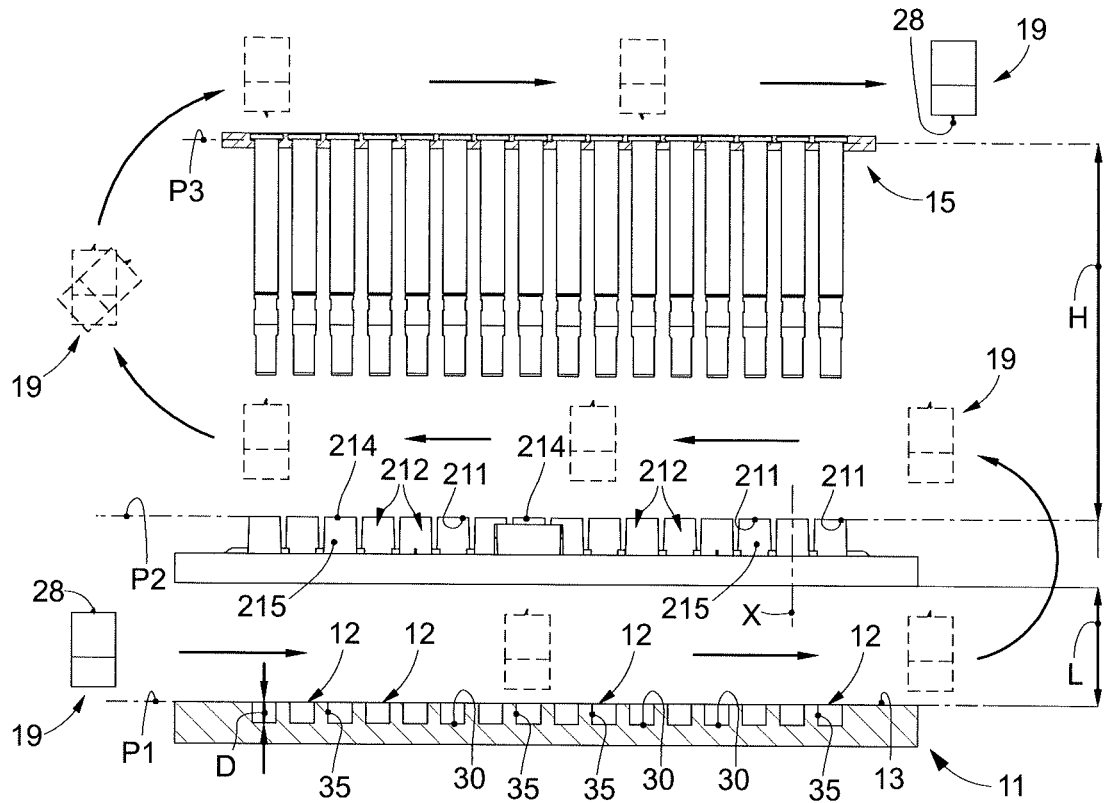
FIG. 14 shows a variant of the operating step shown in FIGS. 8-9, in which there is only one ionizing device which performs a possible ionization path.

Although the presence of several ionizing devices 19, 27 is not strictly necessary, since as shown by way of example in FIG. 14 only one ionizing device 19 would be sufficient, advantageously the presence of a plurality of ionizing devices 19, 27 allows to reduce the neutralization times of the electrostatic charges and therefore allows to increase the overall productivity of the apparatus 10. Furthermore, as shown in FIGS. 14-15, during the movement of the ionizing device 19 it is necessary to provide the correct orientation of the emitters 28 in order to direct the charges in the appropriate directions, this possibly also involving a number of passes to neutralize the charges.

In accordance with some embodiments, a method is provided to neutralize static electricity present on the surface of containers 100 and/or of container-holding trays or nests 200 in which an ordered group of such containers 100 is disposed, each container being received in a seating 212, configured for example as a collar provided with a channel 211, the containers 100 of the ordered group as above occupying the collars 212 according to the positioning matrix M1. The method comprises the following steps:

partly lifting at least one part of the ordered group of containers 100 supported by the container-holding tray or nest 200 with respect to the container-holding tray or nest 200 so as to make a gripping portion of each partly raised container 100 accessible;

inserting an extraction member 15 between the partly raised containers 100, engaging the gripping portion of each container 100 so that the containers 100 are held by the extraction member 15;

extracting the containers 100 held by the extraction member 15 from the container-holding tray or nest 200, reaching a raised condition in which the extraction member 15 maintains the containers 100 extracted stationary in a position such as to leave the seatings 212 of the container-holding tray 200 previously occupied by the containers extracted by the extraction member 15 at least partly free;

neutralizing static electricity present on the surface of the containers 100 in the raised condition described above and/or of the container-holding tray or nest 200, by means of at least one ionizing device 19, by operating a relative motion of the ionizing device 19 with respect to the containers 100 in the raised condition and/or with respect to the container-holding tray 200, along a path that develops in the proximity of the containers 100 in the raised condition and/or of the container-holding tray or nest 200, so as to ionize the surrounding space and neutralize static electricity present on the surface of the containers 100 in the raised condition and/or of the container-holding tray or nest 200.

With reference to FIGS. 1-7, a possible operating sequence of the functioning of the apparatus of FIG. 1 is now described.

When the neutralization of the electrostatic charges on the containers 100 and on the respective container-holding tray or nest 200 is required, before the weighing operation, the container-holding tray or nest 200, which temporarily supports the ordered group of containers 100, is moved vertically, for example with an automated, advantageously robotized, movement device from an operating position of support, FIG. 1, to an inactive, or resting, position, in which the container-holding tray or nest 200 rests statically on the support member 14, FIG. 2.

When the container-holding tray or nest 200 is in the inactive position, temporarily supported by the support member 14 and, at the same time, the containers 100 rest on the respective cavities 12 (in particular supported by their lateral surface 35 and/or by their bottom wall 30), the containers 100 are consequently raised with respect to a plane that is parallel to the plane P2 of the container-holding tray or nest 200, but is through the upper base surface of the collars 212, by a height equal to the lifting overrun P as above, which makes the containers 100 accessible for insertion into the holding seatings 17 of the extraction member 15.

At the same time, the extraction member 15 which is located, for example, in a lateral position with respect to the lower support base 11, to the support member 14 and to the container-holding tray or nest 200, is located or is taken into alignment with the rows or columns of the positioning matrix M1 of the containers 100 previously made available for gripping, FIG. 2.

Subsequently, the extraction member 15 performs a first movement to engage the containers 100 in the holding seatings 17, moving closer to the rows of containers 100 and progressively positioning the arms 16 between such rows of containers 100. In this step, the collar 111 of each container 100 is positioned in correspondence with a holding seating 17 of the extraction member 15, FIG. 3.

Once the correspondence between the support edges or collars 111 of the containers 100 and the holding seatings 17 of the extraction member 15 has been obtained, the containers 100 are in fact held by the holding seatings 17 and, therefore, the extraction member 15 performs a second movement, orthogonal to the first movement, in a vertical direction, completely lifting the containers 100 from the container-holding tray 200 and placing them in a raised position, thus defining the free interspace 18 between the containers 100 and the container-holding tray 200, FIG. 4.

Once the interspace 18 has been defined, the ionizing device 19 and possibly the other ionizing device 27 are moved along paths defined by curved or rectilinear segments so as to sweep the totality, or the almost totality, of the area underneath the containers 100 and above and possibly underneath the support member 14 temporarily supporting the container-holding tray or nest 200, FIG. 4. In particular, in order to guarantee a complete neutralization of the charges, it may be sufficient for the ionizing device 19 and possibly the other ionizing device 27 to sweep the area described above only once. In this case, the speed of movement of the ionizing devices 19, 27 has to be suitably adapted, so that they move more slowly in order to have sufficient time to carry out the neutralization of the charges.

Once the step of neutralizing the electrostatic charges is completed, the extraction member 15 performs a third movement, similar to the second movement as above but in the opposite direction, in order to reposition the containers 100 in the container-holding tray or nest 200 still temporarily resting on the support member 14, FIG. 5. In this step, the base ends 112 of the containers 100 are therefore once again inserted into the respective cavities 12.

Figure 6:
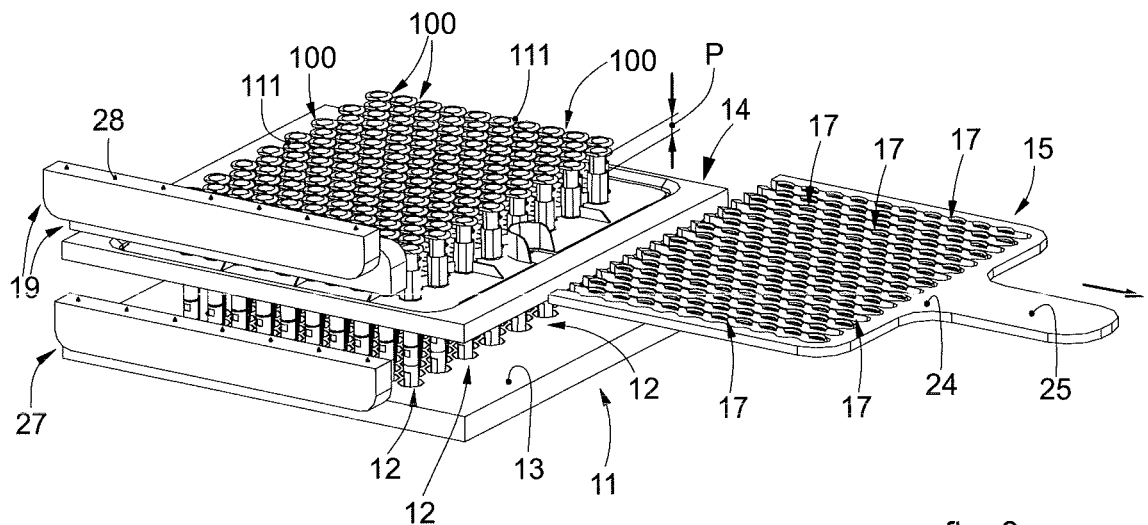
Figure 7:
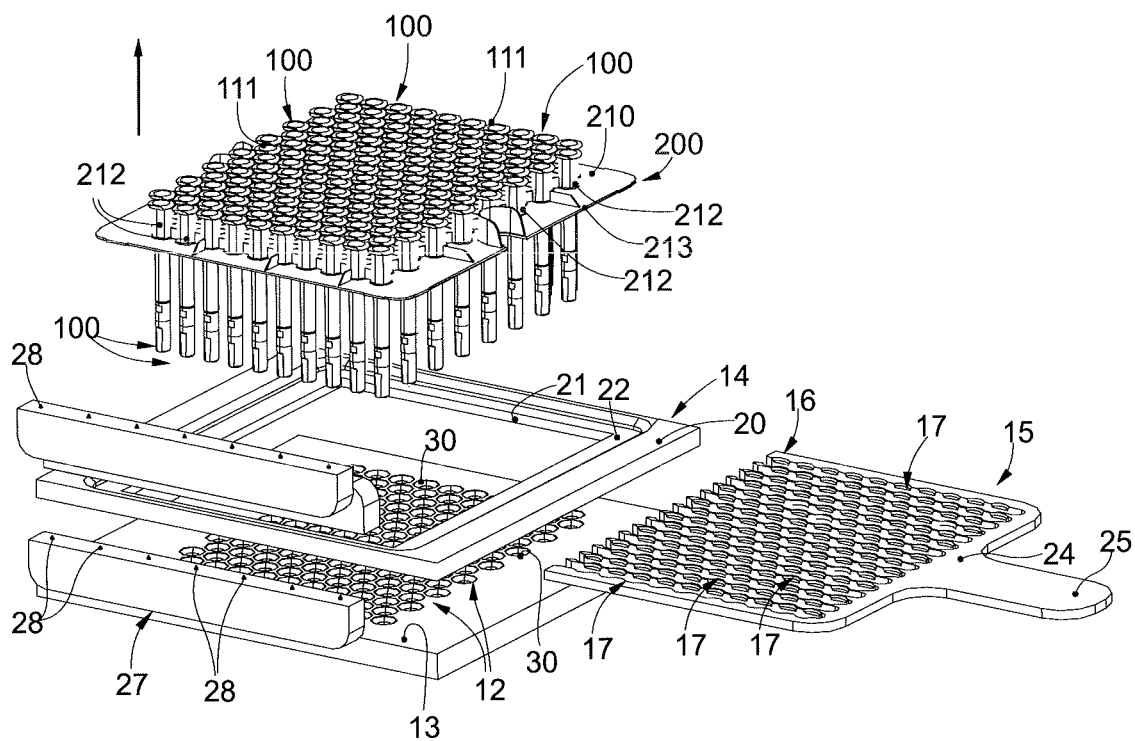

Subsequently, the extraction member 15 is returned to the lateral position, with a movement opposite the first movement as above, FIG. 6, and the container-holding tray or nest 200 is lifted vertically from the inactive position to the operative or support position, FIG. 7, in order to then proceed with the subsequent operations.

In accordance with the embodiment shown in FIG. 15, another possible operating sequence of the functioning of the apparatus of FIG. 1 is described.

In particular, in this case when the extraction member 15 performs a second movement, orthogonal to the first movement, in the vertical direction, it almost completely lifts the containers 100 from the container-holding tray 200, placing them in a raised position in which an end portion of each container, for example the base end 112, remains inside the respective channel 211 of the container-holding tray or nest 200. Subsequently, the at least one ionizing device 19, or the one or more ionizing devices 19, 27, sweeps the area above the containers 100, held in the raised position by the holding gripper 15, and below the container-holding tray or nest 200, temporarily positioned resting on the support member 14, FIG. 15.

Figure 17:
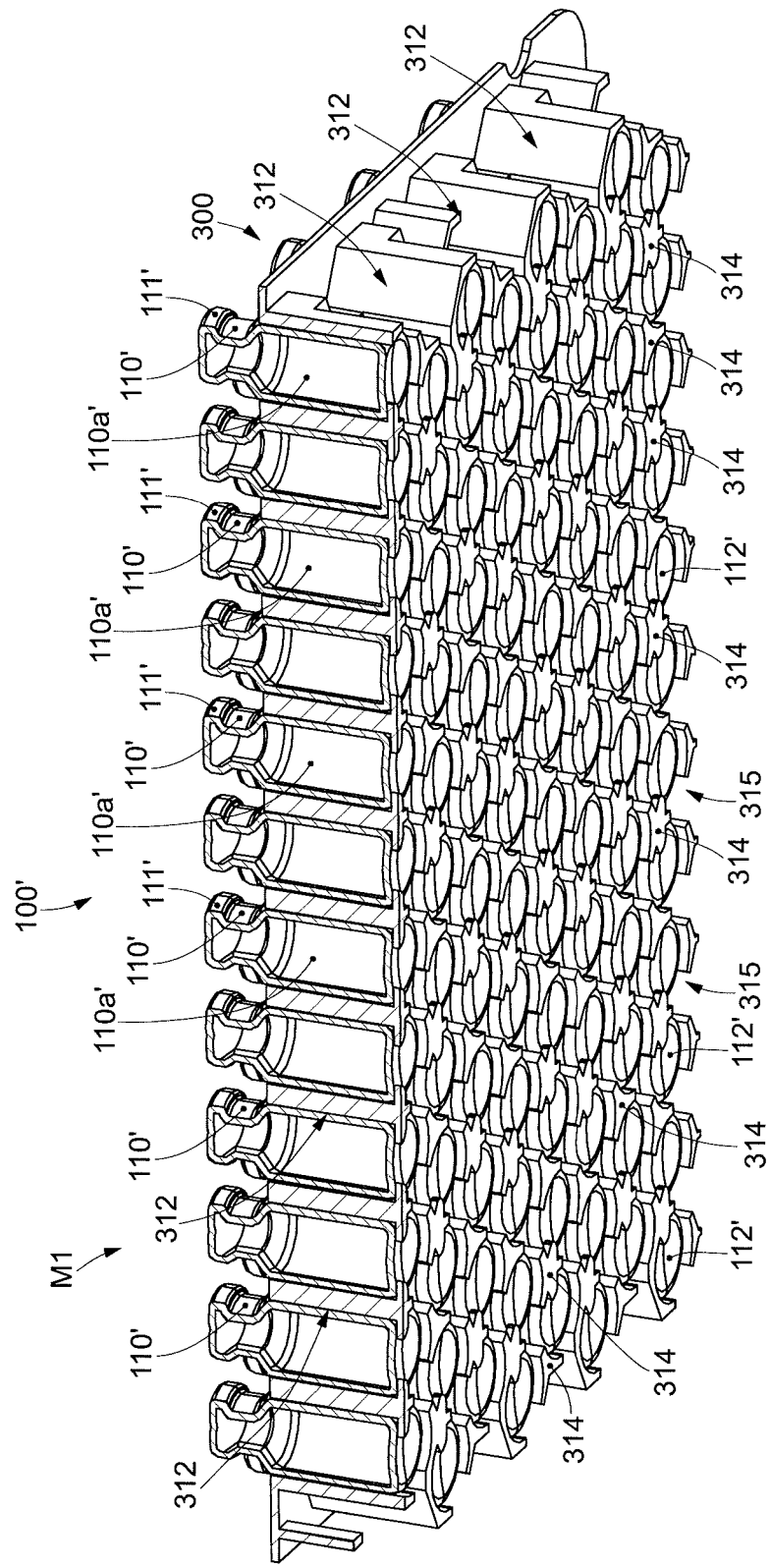
FIG. 17 shows a perspective and partly sectioned view from below of a variant of a container-holding tray that can be used in an apparatus such as that shown in FIG. 1.
Figure 18:
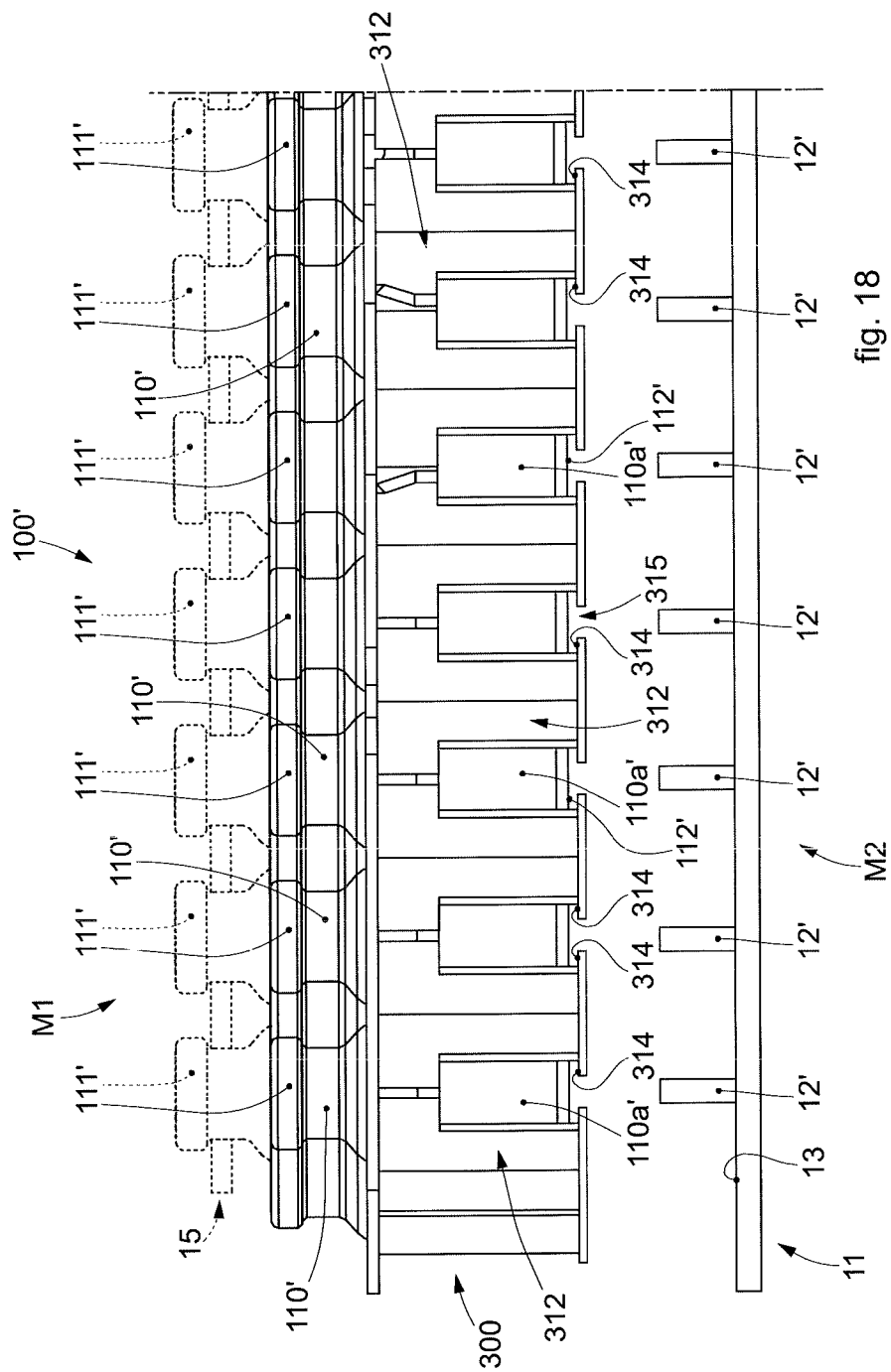
FIG. 18 shows a schematic lateral view of a variant of the apparatus to neutralize static electricity comprising the container-holding tray of FIG. 17

With reference to FIGS. 17 and 18, one variant of the apparatus 10 to neutralize static electricity according to the present invention is described, comprising another embodiment of the container-holding tray, or nest, indicated with reference number 300 in the drawings.

The container-holding tray 300 is shaped and configured to receive a type of containers 100', visible in FIGS. 17-18, where such containers are configured as bottles, having the typical shape of a bottle.

The container 100' is provided with a lateral wall, or sleeve, 110' internally delimiting a chamber 110a' suitable to contain one or more substances and open upward to allow it to be filled.

The container 100' is provided with a collar 111', shaped to rest in the holding seatings 17 of the gripping loops 29 made on the extraction member 15. Unlike the embodiments described above and shown with reference to FIGS. 1-16, in which the containers 100 are configured as syringes, in this case the containers 100' (bottles) are not maintained suspended by their collar 111' on the container-holding tray or nest 300, as clearly shown in FIGS. 17 and 18, but are instead maintained resting from the bottom. The container 100' also comprises a base end 112', positioned on the opposite side with respect to the collar 111'.

Also in these embodiments the containers 100', pre-filled with a substance and pre-positioned, form an ordered group of containers 100' in a container-holding tray 300 according to the same positioning matrix M1 defined above.

Each container 100' is received in a respective seating 312 provided in the container-holding tray 300. The seating 312 is defined as a sort of through channel, inside which the container 100' is disposed.

Each seating 312 comprises a support edge 314 intended to receive, resting on it, the base end 112' with which each container 100' is provided.

Preferably, the container 100' has a transverse size, that is, the external diameter of the lateral wall 110', which is correlated to the size of the seating 312.

The support edge 314 of each seating 312 is defined by at least one projecting portion which projects toward the container 100' so as to engage the base end thereof, in order to support it in respective support zones, which are distanced from each other by a certain arc of circumference in order to guarantee a stable support for the containers 100'. According to some example embodiments, the support edge 314 can be defined by two or three projecting portions, which can be distanced from each other by an arc of circumference subtended respectively, for example, by an angle of about 180° and 120°.

The support edge 314 is therefore configured in such a way as to define a hole 315 so as to maintain the base end 112' accessible from below, which is functional to the operating sequence of functioning, as will be described below.

With reference to FIG. 18, the lower support base 11 can be seen provided with the contrasting surface 13 in order to interact with the ordered group of containers 100 before the extraction member 15 performs the first engagement movement.

According to this variant, the contrasting surface 13 is provided with a plurality of elongated pegs 12' disposed according to the support matrix M2 defined above, corresponding to the positioning matrix M1. It should be noted that the function of the elongated pegs 12' is completely similar to that of the cavities 12 described previously.

During use, a relative movement between the lower support base 11 and the container-holding tray 300 leads each elongated peg 12' to penetrate a respective hole 315 in order to thrust the base end 112' upward, so as to partly extract the containers 100' from the respective seatings 312. In this condition, the containers 100' are taken to the dashed position of FIG. 18 in which they are always maintained resting by the respective seatings 312, inside which there remains a portion of the container that has an extension sufficient to guarantee the containers 100' are held correctly.

Subsequently, the partly extracted containers 100' are picked up by the extraction member 15, schematized in the drawing, so that the collars 111' enter the holding seatings 17 of the gripping loops 29. At this point, it is provided to perform all the steps of the method to neutralize static electricity described previously, which can also be applied to these embodiments described here with reference to FIGS. 17 and 18, with minimal adaptations, which will be completely obvious to the person of skill in the art, due to the presence of the elongated pegs 12' instead of the cavities 12.

In another embodiment, not shown, this variant may be without the lower support base 11 since, as can be seen from FIG. 18, the collars 111' of the containers 100' are accessible to the extraction member 15 even when the containers 100' are housed in the respective seatings 312 and the extraction member 15 is able to engage the collars 111' even if the containers 100' are not extracted from their seatings.

It is clear that modifications and/or additions of parts or steps may be made to the apparatus 10 and method to neutralize static electricity present on the surface of containers and/or container-holding trays as described heretofore, without departing from the field and scope of the present invention.

It is also clear that, although the present invention has been described with reference to some specific examples, a person of skill in the art shall certainly be able to achieve many other equivalent forms of apparatus and method to neutralize static electricity present on the surface of containers and/or container-holding trays, having the characteristics as set forth in the claims and hence all coming within the field of protection defined thereby.

In the following claims, the sole purpose of the references in brackets is to facilitate reading: they must not be considered as restrictive factors with regard to the field of protection claimed in the specific claims.

The invention claimed is:

1. Apparatus to neutralize static electricity present on the surface of containers and/or nests, in which said containers are disposed, said apparatus comprising:
   an ordered group of containers, each container of said ordered group of containers having a body that develops along a main axis of longitudinal extension of the container;
   a nest having a plurality of seatings disposed according to an ordered matrix, each seating being configured to house, resting on it, a respective container of said ordered group of containers, and developing along an axis of symmetry substantially vertical and parallel to, or coincident with, said main axis of the container housed in said seating, the axes of symmetry of said plurality of seatings being reciprocally parallel;
   an extraction member configured to engage at least one part of said ordered group of containers housed in said nest, said extraction member being configured to perform a relative lifting movement with respect to the nest so as to at least partly extract from the respective seatings of said nest said at least one part of said ordered group of containers previously engaged, and to maintain said at least one part of said ordered group of containers extracted from the respective seatings in a raised condition, so that the seatings of said nest, previously occupied by the containers, are left at least partly free;
   at least one ionizing device configured to be relatively mobile with respect to the containers extracted and/or with respect to the nest, while said at least one part of said ordered group of containers extracted is in said raised condition and said nest has the seatings left at least partly free by the respective containers extracted, along a path that develops in the proximity of the containers extracted and/or in the proximity of said nest, so as to ionize the surrounding space and neutralize static electricity present on the surface of the containers in the raised condition and/or of the nest having the seatings left at least partly free by the respective containers extracted, wherein said extraction member comprises one of a plurality of inter-spaced arms, parallel to each other and defining at least one gripping loop, said at least one gripping loop being configured to house the containers, wherein said extraction member is configured to perform, before said relative lifting movement, at least one relative engagement movement with respect to the nest, in order to house said at least one part of said ordered group of containers, laterally aligning said at least one gripping loop with at least one respective row of said ordered matrix of seatings and moving said at least one gripping loop in a direction of engagement, said direction of engagement being transverse with respect to said axes of symmetry of said seatings, so as to house and hold said at least one part of said ordered group of containers in the at least one gripping loop.

2. Apparatus as in claim 1, characterized in that said extraction member is configured to extract at least one part of said ordered group of containers and take it to the raised condition of complete extraction from said seatings of the nest, so as to create a free interspace between the containers extracted and said nest, said at least one ionizing device being configured to be relatively mobile with respect to the containers in the raised condition and/or with respect to the nest along a path that develops in said interspace.

3. Apparatus as in claim 1, characterized in that it comprises a manipulator configured to hold said at least one ionizing device and move it along said path which develops in the proximity of the containers in the raised condition and/or of said nest.

4. Apparatus as in claim 1, characterized in that it comprises a lower support base provided with a contrasting bottom to interact with said ordered group of containers, before said extraction member performs said engagement movement.

5. Apparatus as in claim 4, characterized in that the contrasting bottom is provided with a plurality of cavities disposed according to a support matrixes, corresponding to said positioning matrix, wherein each cavity has a shape substantially mating with the shape of a closed base end, comprised in said body of said containers and opposite an open head end of said body.

6. Apparatus as in claim 4, characterized in that it comprises a support member configured to maintain the nest resting at a predetermined distance with respect to said lower support base, said predetermined distance being chosen so as to obtain the lifting of the group of containers from the nest when said ordered group of containers is in said resting condition on the contrast bottom and said nest is resting on said support member.

7. Apparatus as in claim 6, characterized in that said support member is configured so as to be mobile away from and toward said lower support base, or said lower support base is configured so as to be mobile away from and toward said support member, or both are configured so as to be reciprocally mobile away from and toward each other.

8. Apparatus as in claim 4, characterized in that it comprises at least one further ionizing device configured to be relatively mobile with respect to the containers in the raised condition and/or with respect to the nest along a path that develops in a further free interspace between said nest and the lower support base, when the containers extracted are in said raised condition.

9. Apparatus as in claim 1, characterized in that said at least one ionizing device is configured to be mobile along curved or rectilinear trajectories.

10. Apparatus as in claim 1, characterized in that said arms of said extraction member are stationary.

11. Apparatus as in claim 1, characterized in that each gripping loop comprises an array of holding seatings for said containers disposed in a manner corresponding to said positioning matrix, each holding seating being shaped to support a respective container.

12. Apparatus as in claim 11, characterized in that each holding seating comprises respective support portions, facing each other from opposite sides of a same gripping loop, said support portions being recessed on respective arms in order to receive, resting on them, a respective container.

13. Apparatus as in claim 1, characterized in that each seating has a cylindrical wall which develops around an axis of symmetry and has a predefined longitudinal extension, measured according to a directrix parallel to the axis of symmetry.

14. Method to neutralize static electricity present on the surface of containers and/or nests, in which said containers are disposed, comprising the following steps:
   preparing an ordered group of containers, each container of said ordered group of containers having a body which develops along a main axis of longitudinal extension of the container;
   preparing a nest having a plurality of seatings, disposed according to an ordered matrix, each seating being configured to house, resting on it, a respective container of said ordered group of containers, and developing along an axis of symmetry substantially vertical and parallel to, or coincident with, said main axis of the container housed in said seating, said axes of symmetry of said plurality of seatings being reciprocally parallel;
   preparing an extraction member configured to engage and move at least one part of said ordered group of containers housed in said nest;
   preparing at least one ionizing device configured to be relatively mobile with respect to the containers and/or with respect to the nest;
   extracting at least one part of said group of containers from respective seatings of said nest occupied by said containers resting on them, moving said extraction member with a relative lifting movement with respect to the nest so as to at least partly extract from the respective seatings of said nest said at least one part of said ordered group of containers;
   reaching a raised condition in which said at least one part of said ordered group of containers extracted from the respective seatings is maintained stationary in a position such as to leave the respective seatings of the nest previously occupied by the containers extracted at least partly free;
   neutralizing static electricity present on the surface of the containers in said raised condition and/or of the nest, by means of said at least one ionizing device by operating a relative motion of the ionizing device with respect to the containers extracted and/or with respect to the nest, while said at least one part of said ordered group of containers extracted is in said raised condition and said nest has the seatings left at least partly free by the respective containers extracted, along a path that develops in the proximity of the containers in a raised condition and/or in the proximity of said nest, so as to ionize the surrounding space and neutralize static electricity present on the surface of the containers in the raised condition and of the nest having the seatings left at least partly free by the respective containers extracted;

said method being characterized in that said extraction member is provided with a plurality of inter-spaced arms, parallel to each other and defining at least one gripping loop, said at least one gripping loop being configured to house the containers, and in that before said extracting step it comprises a step of engaging said at least one part of said containers by moving said extraction member with relative movement toward the nest laterally aligning said at least one gripping loop with at least one respective row of said ordered matrix of seatings and moving said at least one gripping loop in a direction of engagement transverse with respect to said axes of symmetry of said seatings, so as to house and hold said at least one part of said ordered group of containers in respective gripping loops in order to then carry out the step of extracting said at least one part of said ordered group of containers housed and held in said at least one gripping loop.

15. Method as in claim 14, characterized in that in said step of preparing a nest, each seating of said plurality of seatings has a cylindrical wall which develops around said axis of symmetry and has a predefined longitudinal extension, measured according to a directrix parallel to the axis of symmetry.

\* \* \* \* \*